United States Patent [19]

Schmitt

[11] Patent Number: 6,094,589
[45] Date of Patent: Jul. 25, 2000

[54] MEDICAL DIAGNOSTIC APPARATUS WITH A CONTROL LIMITED TO USE ONLY BY AN AUTHORIZED PERSON

[75] Inventor: Thomas Schmitt, Forchheim, Germany

[73] Assignee: Siemens Aktiengesellschaft, Munich, Germany

[21] Appl. No.: 08/898,115

[22] Filed: Jul. 22, 1997

[30] Foreign Application Priority Data

Jul. 31, 1996 [DE] Germany ............................ 196 30 951

[51] Int. Cl.[7] ................................................. A61B 19/00
[52] U.S. Cl. ................... 600/407; 382/115; 340/825.31; 128/897; 378/210
[58] Field of Search ........................... 600/407; 128/897, 128/920; 378/204, 208, 210; 382/115–118, 124, 128, 132, 325, 116, 117; 340/825.31, 825.34

[56] References Cited

U.S. PATENT DOCUMENTS

| | | |
|---|---|---|
| 3,737,863 | 6/1973 | Rowland et al. . |
| 3,971,946 | 7/1976 | Craig et al. . |
| 4,107,775 | 8/1978 | Ott . |
| 4,529,870 | 7/1985 | Chaum . |
| 4,821,118 | 4/1989 | Lafreniere . |
| 4,839,806 | 6/1989 | Goldfischer et al. . |
| 4,989,253 | 1/1991 | Liang et al. . |
| 4,991,193 | 2/1991 | Cecil et al. . |
| 4,993,068 | 2/1991 | Piosenka et al. . |
| 5,193,855 | 3/1993 | Shamos . |
| 5,229,764 | 7/1993 | Matchett et al. . |
| 5,303,148 | 4/1994 | Mattson et al. . |
| 5,335,257 | 8/1994 | Stunberg . |
| 5,345,538 | 9/1994 | Narayannan et al. . |
| 5,420,936 | 5/1995 | Fitzpatrick et al. . |
| 5,548,660 | 8/1996 | Lemelson ............................... 382/116 |
| 5,561,699 | 10/1996 | Fenner . |
| 5,654,997 | 8/1997 | Brownell et al. . |
| 5,703,922 | 12/1997 | Rattner . |
| 5,719,950 | 2/1998 | Osten et al. ............................ 382/115 |
| 5,745,046 | 4/1998 | Itsumi et al. . |
| 5,788,688 | 8/1998 | Bauer et al. . |
| 5,838,306 | 11/1998 | O'Connor et al. . |
| 5,857,028 | 1/1999 | Frieling . |
| 5,887,140 | 3/1999 | Itsumi et al. . |

FOREIGN PATENT DOCUMENTS

| | | |
|---|---|---|
| 0 750 880 | 6/1996 | European Pat. Off. . |
| 42 31 913 | 1/1994 | Germany . |

*Primary Examiner*—Marvin M. Lateef
*Assistant Examiner*—Shawna J. Shaw
*Attorney, Agent, or Firm*—Hill & Simpson

[57] ABSTRACT

In a medical diagnostic apparatus, certain functions of the diagnostic apparatus can only be implemented by persons authorized for the operation thereof. To this end, a detector is provided for acquiring a physical feature, for example a fingerprint of the operator, and execution of a function selected by the operator is enabled only when a match with a stored physical feature is found. Among other functions, this allows the brake for the support plate to be released only by the operator and not by the patient.

6 Claims, 2 Drawing Sheets

MEDICAL DIAGNOSTIC APPARATUS WITH A CONTROL LIMITED TO USE ONLY BY AN AUTHORIZED PERSON

BACKGROUND OF THE INVENTION

1. Field of the Invention

The present invention is directed to a medical diagnostic apparatus, such as an X-ray diagnostic apparatus, which has a number of functions which are controlled by the actuation of control elements.

2. Description of the Prior Art

A medical diagnostic apparatus such as an X-ray diagnostic apparatus conventionally has an exposure unit composed of an X-ray radiator and a radiation receiver and the capability of controlling the voltage supply for the radiation transmitter for generating X-rays, and possibly also the capability to control an electronic image-generating system. The functions for generating the radiation and for generating an image from the signals that proceed from a radiation detector given transirradiation of an examination subject are usually selected and adjusted by respective switches or knobs on a control panel. It is not always desirable that all functions can be executed by arbitrary operating personnel.

Such an X-ray diagnostic apparatus can also have a support arrangement for an examination subject having an adjustable support plate. The support plate is then preferably arrested by a brake that can be released by the actuation of a switch. It is possible that the examination subject (patient) may inadvertently actuate this switch when getting off the support plate, so that there is the risk that the support plate is unintentionally caused to move and the patient may fall from the support plate.

For example, European Application 0 463 187 discloses an X-ray diagnostic apparatus with such a support plate and control arrangement.

SUMMARY OF THE INVENTION

It is an object of the present invention to provide a medical diagnostic apparatus of the type described above wherein certain functions can only be triggered by a selected group of persons (authorized personnel).

The above object is achieved in accordance with the principles of the present invention in a medical diagnostic apparatus which has a detector for acquiring a physical feature, such as a fingerprint, of an operator, and an evaluation stage which evaluates the signals from the detector before enabling execution of a function selected by the operator, so as to assure that the operator is a person who is authorized to implement the selected function. The evaluation stage includes a comparator which compares the signals from the detector to stored data, representing physical features of authorized personnel. Given coincidence between the signal from the detector and a stored dataset, the evaluation stage enables implementation of the selected function.

It is a particular advantage that the brake for the support plate can only be released when the evaluation of the physical feature shows that the operator is authorized. The examination subject can thus touch the switch for releasing the brake without the brake actually being released as a result thereof.

DESCRIPTION OF THE PREFERRED EMBODIMENTS

Figure 1:
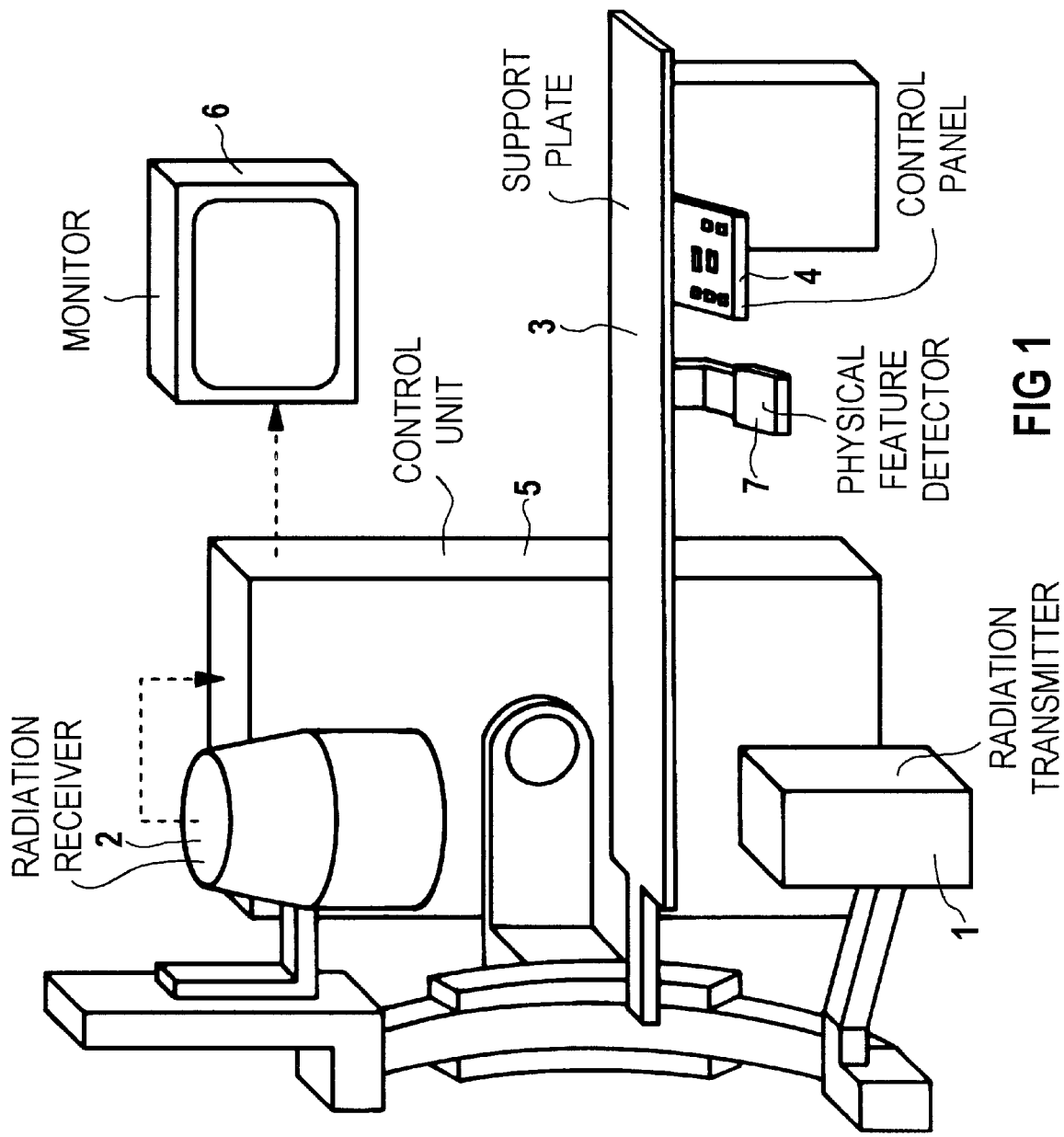
FIG. 1 illustrates an X-ray diagnostic apparatus constructed in accordance with the principles of the present invention, shown schematically.

The inventive medical apparatus will be described herein in the context of the exemplary embodiment of an X-ray diagnostic apparatus. The X-ray diagnostics apparatus shown in FIG. 1 has an exposure unit composed of a radiation transmitter 1 and a radiation receiver 2. In the exemplary embodiment, the radiation receiver 2 is fashioned as an image intensifier; however, it can also be implemented as X-ray film or as a radiation detector that is arranged in the region of a support plate 3 for an examination subject. The support plate 3 can be adjusted in position along its longitudinal and transverse axes and can be arrested via brakes.

Figure 2:
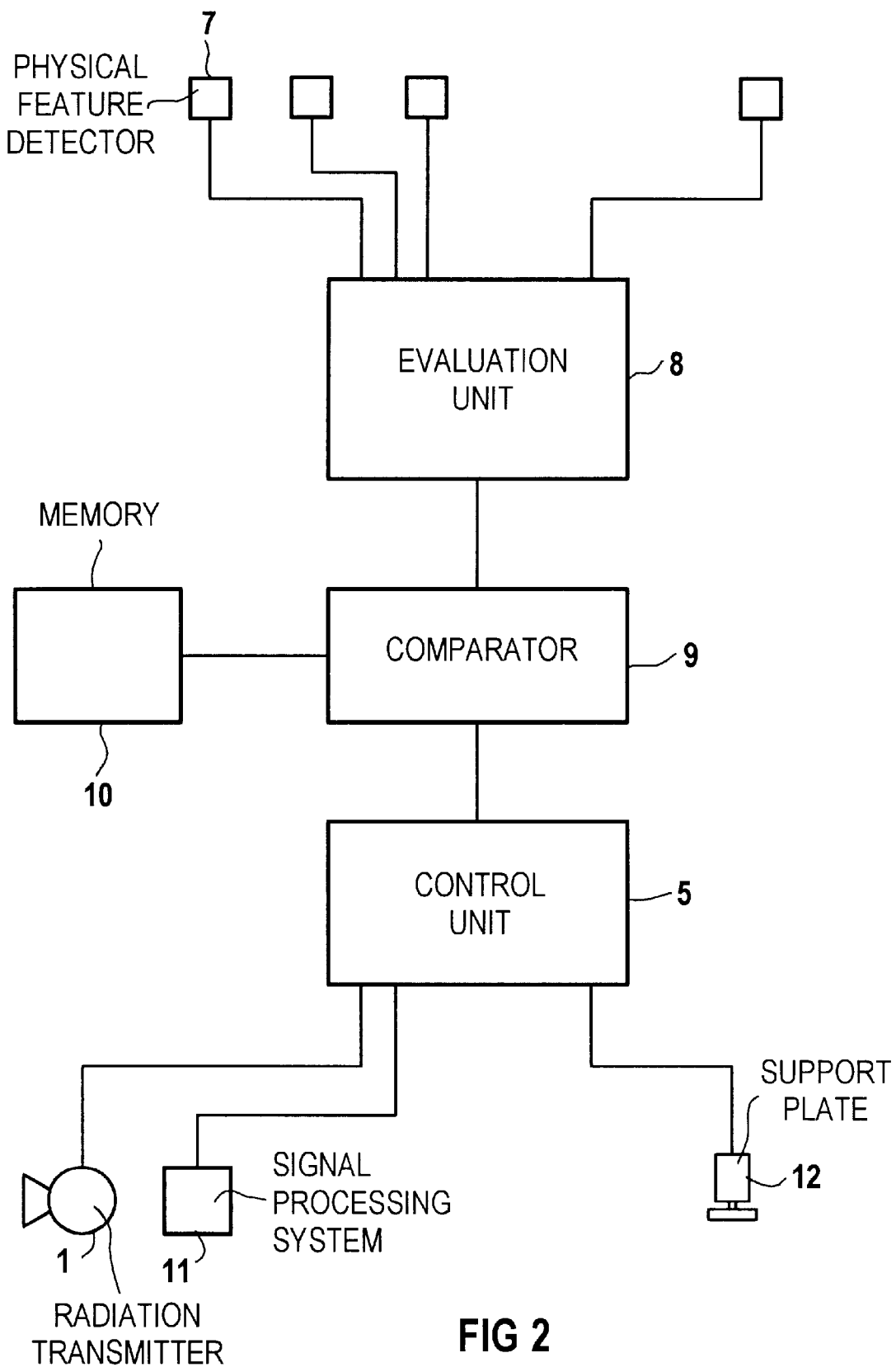
FIG. 2 is a block circuit diagram of the X-ray diagnostics apparatus according to FIG. 1.

The radiation transmitter 1 can be enabled for the emission of radiation via a control panel 4 that has one or more control elements that, when actuated, act on a control unit 5. By means of an image processing system 11 (FIG. 2), a fluoroscopic image of the examination subject can be produced on a monitor 6 from the signals of the radiation receiver 2 acquired upon transirradiation. At least one detector 7 for acquiring a physical feature of an operator, for example for the acquisition of a fingerprint, is inventively provided at or in the region of the control panel 4. As can be seen from FIG. 2, the signals from the detector 7 are supplied to an evaluation unit 8 that is followed by a comparator 9. The comparator 9 compares the signals received from the evaluation unit 8 to signals stored in a memory 10 that were obtained from at least one operator authorized for the operation of the X-ray diagnostics apparatus. When coincidence is recognized, then the comparator 9 emits a signal to the control unit 5, so that at least one function allowed to be implemented by this specific operator is enabled and can be executed. It can be provided that only a specific person can trigger emission of radiation by the radiation transmitter 1, and this person or only some other operator may be authorized for the operation of the image processing system 11.

The inventive embodiment of the X-ray diagnostics apparatus is especially advantageous when brakes 12 for producing or releasing an arrest of the support plate 3 can only be actuated by the operating personnel. It is thus assured that the brakes 12 cannot be released when an examination subject inadvertently comes into contact with the switch element for releasing the brake 12.

Further components of the X-ray diagnostics apparatus, of course, can also be correspondingly operated in this manner within the scope of the invention.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical diagnostic apparatus comprising:
   a plurality of components comprising means for conducting a medical procedure including at least one function-performing component;
   a manually actuatable actuation element which, when actuated, causes execution of a function by the function-performing component, said function comprising a part of said medical procedure;
   detector means for acquiring a physical feature of an operator who actuates said actuation element;

memory means for storing data representing said physical feature for an operator who is authorized to implement said function;

comparator means for comparing a signal from said detector means representing the physical feature of said operator with said data in said memory means and for emitting an enable signal given coincidence of said data represented by said signal from said detector and data stored in said memory means; and control means for enabling execution of the function caused by actuation of said actuation element only upon receipt of said enable signal, and for otherwise automatically inhibiting execution of said function.

2. A medical diagnostic apparatus as claimed in claim 1 wherein said detector means comprises means for detecting a fingerprint of said operator as said physical feature, and wherein said memory means comprises means for storing data representing fingerprints of respective operators authorized to implement said function.

3. A medical diagnostic apparatus as claimed in claim 1 wherein said function-performing component comprises a brake for a patient support plate.

4. A medical diagnostic apparatus as claimed in claim 1 wherein said function-performing component comprises a radiation transmitter.

5. A medical diagnostic apparatus as claimed in claim 4 wherein said radiation transmitter comprises an X-ray source.

6. A medical diagnostic apparatus as claimed in claim 1 wherein said function-performing component comprises a signal processing chain for analyzing diagnostic signals obtained from an examination subject.

* * * * *